United States Patent
Stewart et al.

(10) Patent No.: US 6,485,469 B1
(45) Date of Patent: Nov. 26, 2002

(54) SHIELDED DENTAL SAFETY NEEDLE

(75) Inventors: Bradley M. Stewart, O'Fallon, MO (US); Eugene E. Weilbacher, Ellisville, MO (US)

(73) Assignee: Sherwood Services AG, Schaffhausen (CH)

( * ) Notice: Subject to any disclaimer, the term of this patent is extended or adjusted under 35 U.S.C. 154(b) by 121 days.

(21) Appl. No.: 09/757,977

(22) Filed: Jan. 10, 2001

(51) Int. Cl.$^7$ ................................................ A61M 5/00
(52) U.S. Cl. .................... 604/198; 604/192; 604/263
(58) Field of Search .......................... 604/181, 187, 604/192, 198, 263

(56) References Cited

U.S. PATENT DOCUMENTS

| | | | |
|---|---|---|---|
| 4,655,751 A | 4/1987 | Harbaugh | |
| 4,695,274 A | 9/1987 | Fox | |
| 4,723,943 A | 2/1988 | Spencer | |
| 4,767,413 A | 8/1988 | Haber et al. | |
| 4,772,272 A | 9/1988 | McFarland | |
| 4,813,426 A | 3/1989 | Haber et al. | |
| 4,816,022 A | 3/1989 | Poncy | |
| 4,842,587 A | 6/1989 | Poncy | |
| 4,892,107 A | 1/1990 | Haber | |
| 4,917,669 A | 4/1990 | Bonaldo | |
| 5,045,066 A | 9/1991 | Scheuble et al. | |
| 5,070,885 A | 12/1991 | Bonaldo | |
| 5,104,386 A | * 4/1992 | Alzain | 604/198 |
| 5,120,311 A | 6/1992 | Sagstetter et al. | |
| RE34,045 E | 8/1992 | McFarland | |
| 5,219,333 A | 6/1993 | Sagstetter et al. | |
| 5,254,100 A | 10/1993 | Huband | |
| 5,318,541 A | 6/1994 | Altschuler | |
| 5,403,288 A | 4/1995 | Stanners | |
| 5,498,244 A | 3/1996 | Eck | |
| 5,514,107 A | 5/1996 | Haber et al. | |
| 5,520,654 A | 5/1996 | Wahlberg | |
| 5,522,812 A | 6/1996 | Talonn et al. | |
| 5,554,130 A | * 9/1996 | McDonald et al. | 604/198 |
| 5,607,402 A | 3/1997 | Dufresne et al. | |
| RE35,539 E | 6/1997 | Bonaldo | |
| 5,695,475 A | 12/1997 | Best, Jr. et al. | |
| 5,891,098 A | * 4/1999 | Huang | 604/198 |

FOREIGN PATENT DOCUMENTS

| WO | WO 89/04141 | 5/1989 |
|---|---|---|

* cited by examiner

*Primary Examiner*—J. Casimer Jacyna
(74) *Attorney, Agent, or Firm*—Mark S. Leonardo; Peter B. Sorell; Brown Rudnick Berlack Israels LLP

(57) ABSTRACT

A needle cannula apparatus is provided which includes a needle hub that is mountable to an instrument and has a cantilevered portion extending therefrom. The cantilevered portion has a button member and a hub stop disposed at a distal end thereof. The needle hub defines at least one tab slot having a tab slot end. A shield is movably disposed about the needle hub and defines a shield slot configured for relative slidable movement of the button member therein. The shield slot includes a proximal enlarged slot section configured to engage the hub stop such that proximal movement of the shield is prevented. The shield further includes at least one tab stop that is configured for movement within the at least one tab slot of the needle hub and engagement with the tab slot end such that distal movement of the shield is prevented. The needle cannula hub may include at least one hub slot and the shield includes at least one shield rail. The at least one shield rail sidably engages the at least one hub slot facilitating axial movement of the shield relative to the needle hub. The shield slot may further define a transport enlarged slot section disposed between a distal portion of the shield slot and the proximal enlarged slot section. A method for transport and use of the needle cannula apparatus is disclosed.

27 Claims, 6 Drawing Sheets

SHIELDED DENTAL SAFETY NEEDLE

BACKGROUND

1. Technical Field

The present disclosure generally relates to the field of safety needles, and more particularly, to a shielded dental safety needle for protecting practitioners from inadvertent needle contact during the transport, use and disposal of the safety needle.

2. Description of the Related Art

Medical and dental syringes contaminated with body fluids containing infectious diseases, viruses, contaminants, etc., present serious safety hazards to practitioners because of accidental contact with needles. A particular danger exists during attachment and removal of a needle from a syringe. A number of different devices have been proposed to minimize the possibility of spreading infectious disease due to accidents related to inadvertent needle stick injuries.

Typically, to reduce such safety hazards, an extendable needle shield is provided which, after the syringe has been used, can be pushed to an extended position to cover the needle. This prevents an individual from accidentally contacting the needle. Such construction commonly features a shield which locks when pushed to an extended position so that it cannot be retracted to expose the needle, except by application of extraordinary force. A number of such constructions have been proposed to satisfy a general requirement that the needle be permanently covered after use. Some of these constructions involve complex locking mechanisms when the shield is fully extended. For example, U.S. Pat. No. 4,767,413 to Haber et al. disclose a disposable dental syringe having a spring loaded mechanism to enclose a needle after use. These types of devices are not typically adaptable to standard reusable metal dental syringes and, therefore, require costly modifications to the syringes.

Another type of dental syringe having a protective needle shield is disclosed in U.S. Pat. No. 5,522,812 to Talonn et al., the entire contents of which are incorporated herein by reference. Talonn et al. show a tubular shield having one or more elongated keys which are rotated on a collar keyway to a locked position that prevents retraction of the shield. These types of devices are not easily deployed and locked with one hand because they must be rotated to a locked position. This drawback can require two-handed operability increasing the probability of accidental contact with the needle. See also U.S. Pat. Nos. 4,723,943 to Spencer and 5,254,100 to Huband.

Practitioners often use a single syringe to administer additional medication to a medical or dental patient after a first dose has been administered. Some known needle shield devices provide a temporary lock to prevent accidental needle sticks in between uses of the syringe. Spencer discloses a shield that can be rotated to a temporary lock position. The necessary rotation of these type devices is difficult with one-handed operation and, therefore, may require two-handed operation. Further, these devices do not include structure that prevents inadvertent disengagement from the temporary lock positions. These disadvantages increase the possibility of accidental contact with the needle.

Therefore, a need exists for a needle cannula apparatus having a shield that prevents inadvertent needle stick during attachment, general use and removal of a needle cannula from the needle cannula apparatus with one-handed operation. The needle cannula apparatus can also prevent inadvertent needle stick during transport and between injections. Desirably, the needle cannula apparatus has a shield that coaxially aligns a needle therewith and provides a needle straightening feature. Most desirably, the needle cannula apparatus has a shield fabricated from a transparent material whereby the shield prevents impairment and/or fogging of the transparency of the shield.

SUMMARY

Accordingly, the present disclosure provides a needle cannula apparatus and related methods designed to shield, such as, for example, hypodermic and dental needles and protect practitioners from accidental contact with a needle during use and related operations of the needle cannula apparatus. These uses and related operations include attachment and removal of the needle from a syringe, handling of a syringe, etc.

The needle cannula apparatus disclosed has a shield that prevents inadvertent needle stick during attachment, general use and removal of a needle cannula from the needle cannula apparatus with one-handed operation. The needle cannula apparatus may also prevent inadvertent needle stick during transport and between injections. Transport includes such activities as preparation, carrying, etc., for mounting with a syringe, packaging, delivery to a location, retrieval from storage, etc. Desirably, the needle cannula apparatus has a shield that coaxially aligns a needle therewith and provides a needle straightening feature. Most desirably, the needle cannula apparatus has a shield fabricated from transparent material whereby the design of the shield prevents impairment and/or fogging of the transparency of the shield.

In one particular embodiment, a needle cannula apparatus is provided, in accordance with the present disclosure. The needle cannula apparatus includes a needle hub that is mountable to an instrument. The needle cannula apparatus has a cantilevered portion extending therefrom. The cantilevered portion has a button member and a hub stop disposed at a distal end thereof. The needle hub defines at least one tab slot having a tab slot end.

A shield is movably disposed about the needle hub and defines a shield slot configured for relative slidable movement of the button member therein. The shield slot includes a proximal enlarged slot section configured to engage the hub stop such that proximal movement of the shield is prevented. The shield further includes at least one tab stop that is configured for movement within the at least one tab slot of the needle hub and engagement with the tab slot end such that distal movement of the shield is prevented.

The needle hub may include a needle cannula coaxially mounted therewith. The needle hub may include an engagement portion configured for releasably mounting the needle hub with the instrument. The needle hub can include a proximal portion that defines an aperture having an internally or externally threaded portion or a self-threading portion configured for releasably mounting the instrument therewith. Alternatively, the needle cannula hub includes at least one hub slot and the shield includes at least one shield rail. The at least one shield rail slidably engages the at least one hub slot facilitating axial movement of the shield relative to the needle hub. Desirably, the needle hub has three hub slots and the shield has three corresponding shield rails. Most desirably, the needle hub defines two diametrically spaced tab slots and the shield further includes two diametrically spaced tab stops.

In an alternate embodiment, the proximal enlarged slot section of the shield slot is defined at a proximal portion thereof and the shield slot further defines a transport enlarged slot section disposed between a distal portion of the shield slot and the proximal enlarged slot section. The transport enlarged slot section can be configured to releasably engage the hub stop such that axial movement of the shield is prevented. The button member may be manipulable to facilitate release of the hub stop from engagement with the transport enlarged slot section facilitating axial movement of the shield.

The shield can have a range of movement between a distal position whereby a distal end of the needle hub including a needle cannula is shielded and a proximal position whereby the distal end of the needle hub including a needle cannula is fully extended. In the distal position, the hub stop can engage the proximal enlarged slot section such that proximal movement of the shield is prevented. In another embodiment, the range of movement includes a transport position whereby the transport enlarged slot section is configured to engage the hub stop such that axial movement of the shield is prevented. The button member may be manipulable to release the hub stop from the transport enlarged slot section facilitating axial movement of the shield. The button member may be releasably lockable in the transport position.

In another alternate embodiment, the shield has an inner surface formed at a distal portion thereof. The inner surface is configured to engage a distal end of the needle hub to facilitate coaxial alignment of the distal end of the needle hub with the shield. The shield can be fabricated from a substantially transparent material, such as, for example, clear polycarbonate, acrylic, etc.

The shield may also include a button cover disposed about the proximal enlarged slot section which is configured to prevent disengagement of the hub stop and the proximal enlarged slot section. The needle hub and the shield can engage to maintain the shield in the proximal position by a friction fit formed therebetween.

The shield may have an inner surface formed at a distal portion thereof. The inner surface engages the needle hub in a configuration to substantially prevent collection of substances that impair the transparency of the shield. This configuration advantageously facilitates viewing of volumetric markings in the syringe, carpule contents and flashback. Moisture from the patent's mouth can become trapped within a shield/hub interface creating a dangerous condition for the patient and/or the practitioner. By providing structure that blocks the path of the moisture from the patient's mouth to the inside of the shield, the occurrence of fogging may be eliminated or greatly reduced.

A method for transport and use of a needle cannula apparatus is provided. The method including the steps of: providing the needle cannula apparatus, similar to those described above; mounting a needle cannula to the needle hub; manipulating the button member within the shield slot to position the shield in a transport position to temporarily prevent axial movement of the shield; mounting the instrument to the needle cannula apparatus; and transporting the needle cannula apparatus. The method may further include the steps of: manipulating the button member to release the shield from the transport position; and manipulating the shield to a proximal position whereby the needle cannula is fully extended from a distal opening of the shield.

The method may further include the steps of: inserting the needle cannula into a subject; removing the needle cannula from the subject; and manipulating the shield to a transport position to temporarily prevent axial movement of the shield. The method can further include the steps of: manipulating the button member to release the shield from the transport position; and manipulating the button member within the shield slot to position the shield in a distal position to fixedly prevent axial movement of the shield.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may best be understood by reference to the following description, taken in connection with the accompanying drawings, in which:

DETAILED DESCRIPTION OF THE EXEMPLARY EMBODIMENTS

The exemplary embodiments of the apparatus and methods of operation disclosed are discussed in terms of safety needles, and more particularly, in terms of shielded dental safety needles and associated syringe components for protecting practitioners and related personnel from inadvertent needle contact during the transport, use and disposal thereof. It is envisioned, however, that the present disclosure will find application to a wide variety of safety needles, cannula needles, syringe components, etc., including dental, phlebotomy, orthopedic, digestive, intestinal, urinary and veterinary types, etc. It is also herein contemplated that the present disclosure finds application to the injection of preventative medication, medicaments, etc., and the collection of blood and fluids from a subject.

In the discussion which follows, the term "proximal" will refer to the portion of a structure which is closer to the practitioner, while the term "distal" will refer to the portion which is further from the practitioner. As used herein, the term "subject" refers to a patient who receives injections or has blood and/or other fluids collected therefrom using the needle cannula apparatus according to the present disclosure. The term "practitioner" refers to an individual administering an injection, performing fluid collection, installing or removing a needle from a syringe using the needle cannula apparatus according to the present disclosure, and may include related personnel.

The following discussion includes a description of a needle cannula apparatus, followed by a description of a method of operating the needle cannula apparatus in accordance with the present disclosure. Reference will now be made in detail to the exemplary embodiments of the disclosure, which are illustrated in the accompanying figures.

Figure 1:
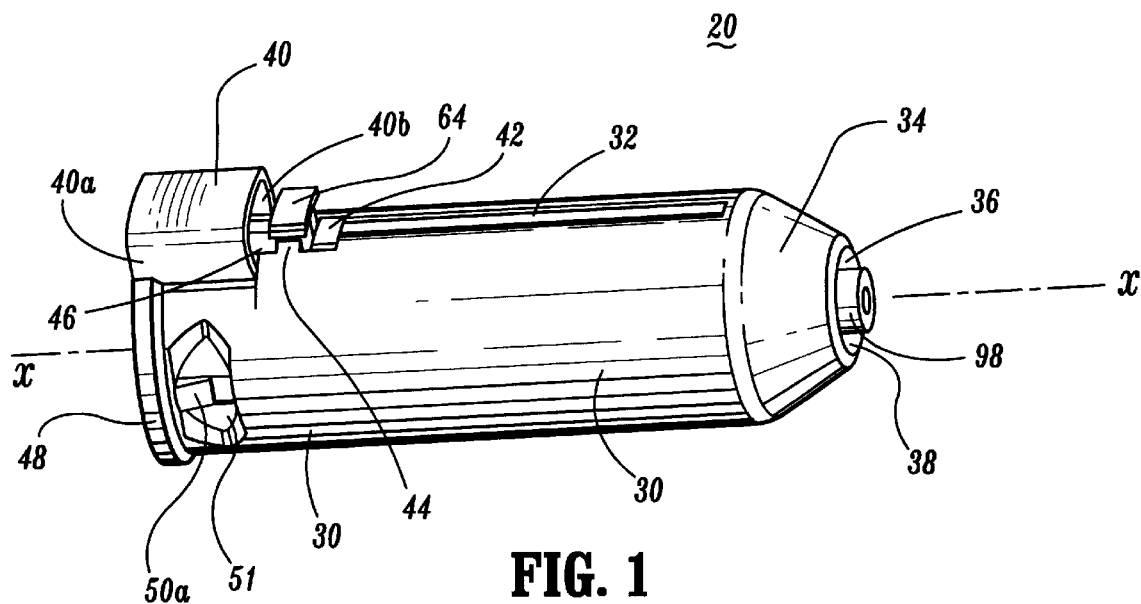
FIG. 1 is a side perspective view illustrating one particular embodiment of a needle cannula apparatus in accordance with the present disclosure.

Turning now to the figures wherein like components are designated by like reference numerals throughout the several views. Attention is initially directed to FIGS. 1 and 2 which illustrate a needle cannula apparatus, such as, for example, a shielded safety needle 20, in accordance with the present disclosure. Shielded safety needle 20 includes a sliding outer shield 30 having a distal frustoconical or tapered shield crown 34. The narrow, low profile design of sliding outer shield 30 allows access to difficult to reach and restricted areas of a patient's body areas. It is contemplated that outer shield 30 may have other configurations that provide access.

Outer shield 30 is movably disposed about a needle hub, discussed below. The needle hub is mountable to an instrument, such as, for example, a syringe. Outer shield 30 and the needle hub cooperate to advantageously shield needles and protect practitioner's from accidental contact with a needle during use, including transport, between injections, etc.

Shielded safety needle 20 is integrally assembled of its consistent components which are molded from flexible polymerics. It is contemplated that semi-rigid and rigid materials may be used including various metals, etc., depending on the particular dental and/or medical application. One skilled in the art, however, will realize other materials and fabrication methods suitable for assembly and manufacture, in accordance with the present disclosure, also would be appropriate.

Shield crown 34 includes a distal opening 36 at a distal portion thereof. Distal opening 36 extends through an interior portion of shield crown 34 and opens into an internal cavity of outer shield 30. An inner surface, such as, for example, cylindrical section 38 extends longitudinally inward from shield crown 34 into the internal cavity. Cylindrical section 38 is configured to engage a distal end of the needle hub, such as, for example, a needle cannula, to facilitate coaxial alignment of the distal end of the needle hub with outer shield 30. Cylindrical section 38 advantageously guides and straightens needle cannulas which may be bent or deformed. This configuration facilitates a properly guided injection, etc.

Figure 1A:
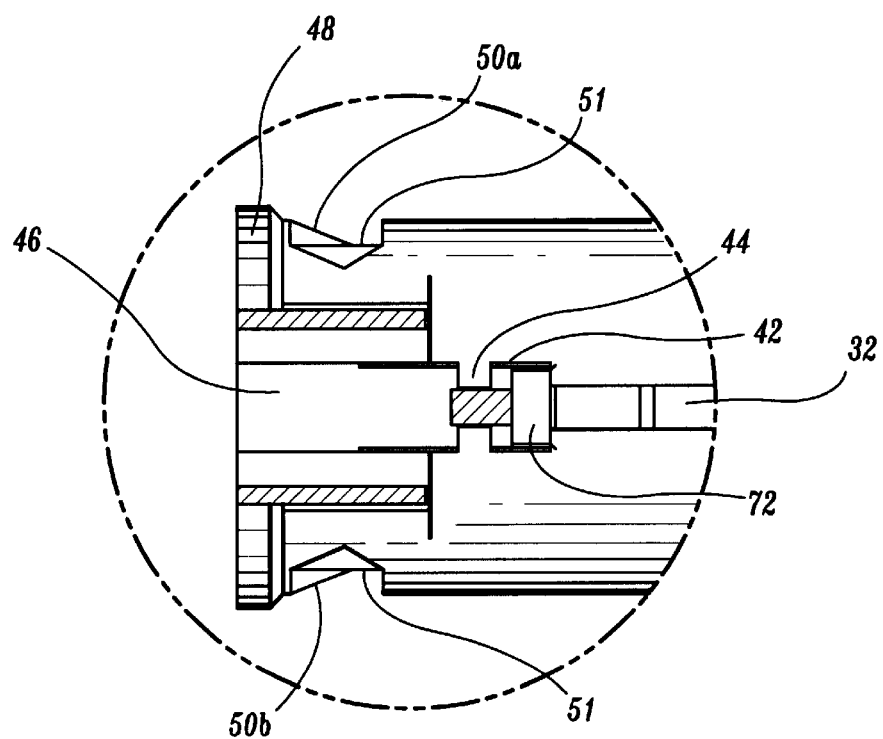
FIG. 1A is a top elevation view, in part cross-section, of a proximal portion of the needle cannula apparatus shown in FIG. 1.

A shield slot 32 extends longitudinally, along a longitudinal axis x of outer shield 30, from shield crown 34 to a proximal end of outer shield 30. As can best be seen in FIG. 1A, shield slot 32 includes a transport enlarged slot section 42 which is in communication with a proximal enlarged slot section 46 through an intermediary narrow area, such as, for example, a section 44. Proximal enlarged slot section 46 is open at its proximal end and intersects the proximal end of a shield lip 48 circumferentially spaced about outer shield 30.

Referring back to FIG. 1, a protruding button cover 40 having side walls 40a and 40b is formed along a proximal end of outer shield 30. Button cover 40 is disposed about the proximal portion of shield slot 32 including proximal enlarged slot section 46. It is envisioned that button cover 40 encloses at least a portion of proximal enlarged slot section 46. Shield lip 48 protrudes outward circumferentially from the proximal periphery of outer shield 30. Shield lip 48 has two ends that integrate with side walls 40a and 40b of button cover 40. Shield lip 48 is not required to protrude from the portion of the proximal periphery that is overlapped by button cover 40.

Outer shield 30 further includes apertures 51 formed along its proximal periphery. Apertures 51 further include tab stops 50a and 50b (FIG. 1A) which are integrally formed with outer shield 30. Tab stops 50a and 50b are cantilevered and cross the boundary defined by the circumferential wall of outer shield 30 so as to protrude within an inner periphery of outer shield 30. Apertures 51 are provided to facilitate molding of cantilevered tab stops 50a and 50b. Tab stops 50a and 50b may be alternatively configured as inwardly protruding snap arms or internal protrusions without departing from the scope of the present disclosure.

Figure 2:
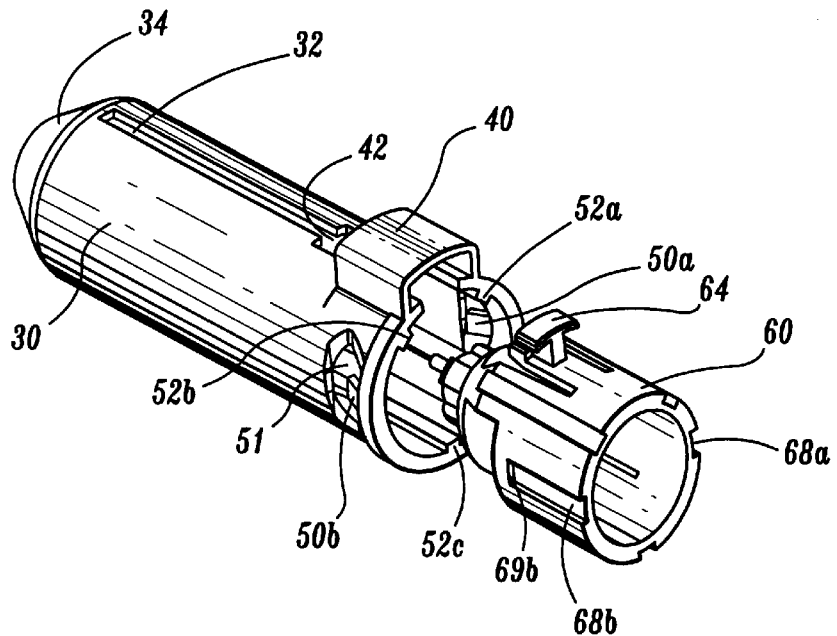
FIG. 2 is a rear perspective view illustrating the needle cannula apparatus shown in FIG. 1, with parts separated.
Figure 2A:
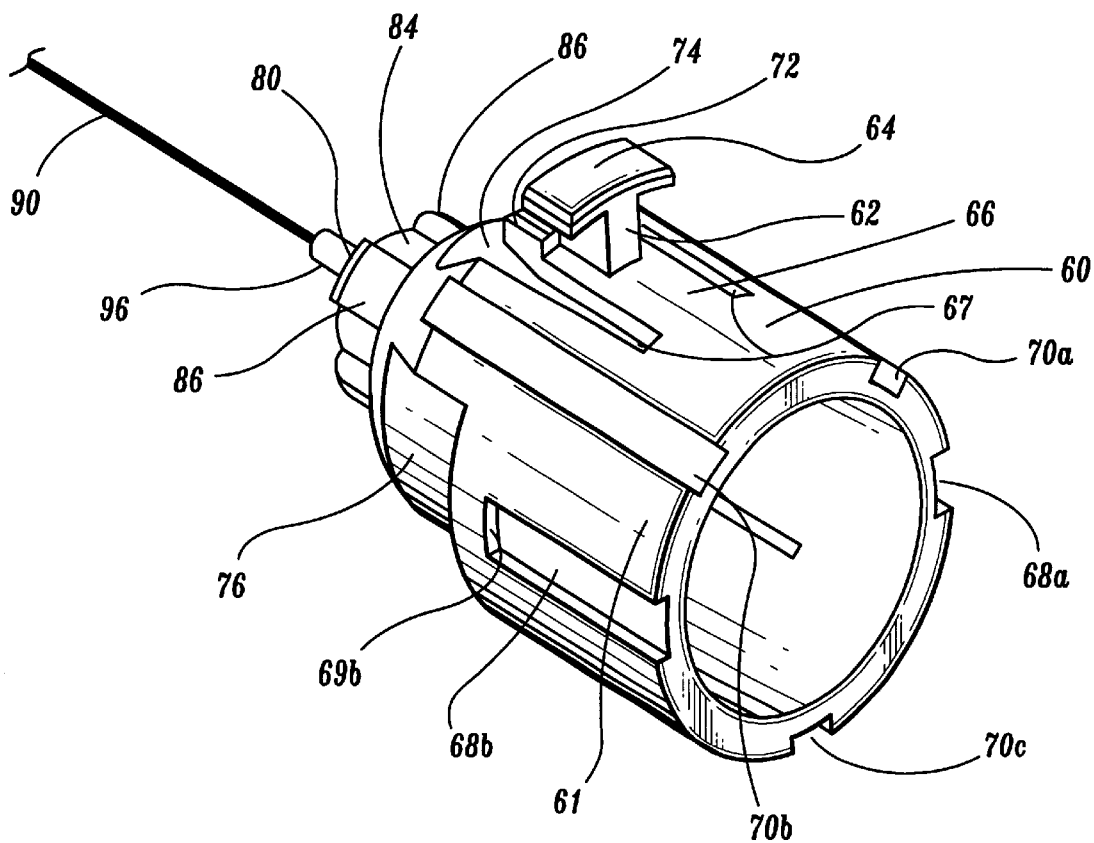
FIG. 2A is an enlarged rear view of a needle hub of the needle cannula apparatus shown in FIG. 1.

Referring to FIGS. 2 and 2A, outer shield 30 includes inner shield rails 52a, 52b and 52c formed along the inner periphery of outer shield 30 and extending longitudinally from the proximal end of outer shield 30 to distal shield crown 34. Inner shield rails 52a, 52b and 52c are spaced apart to longitudinally guide and facilitate axial sliding movement of shield 30 relative to an inner needle hub 60. Inner shield rails 52a, 52b and 52c slideably engage hub slots 70a, 70b and 70c, respectively, correspondingly positioned along an outer periphery of inner needle hub 60.

Inner needle hub 60 includes a proximal hub portion 61, an intermediate crown portion 76 and a distal crown portion 80. Proximal hub portion 61 includes hub slots 70a, 70b and 70c which extend along the entire length of proximal hub portion 61 to slide along inner shield rails 52a, 52b and 52c of outer shield 30. Although three rails and hub slots are illustrated and disclosed, varying numbers of rail/slot configurations may provide sufficient longitudinal guidance for sliding engagement of outer shield 30 and inner needle hub 60.

Figure 4:
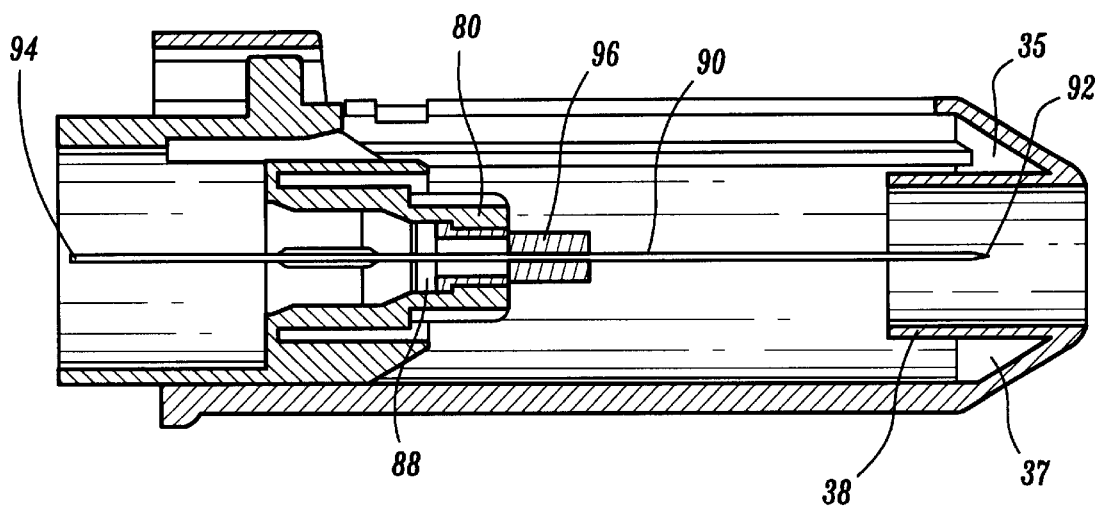
FIG. 4 is an enlarged side cross-sectional view illustrating the needle cannula apparatus in a proximal position.
Figure 4A:
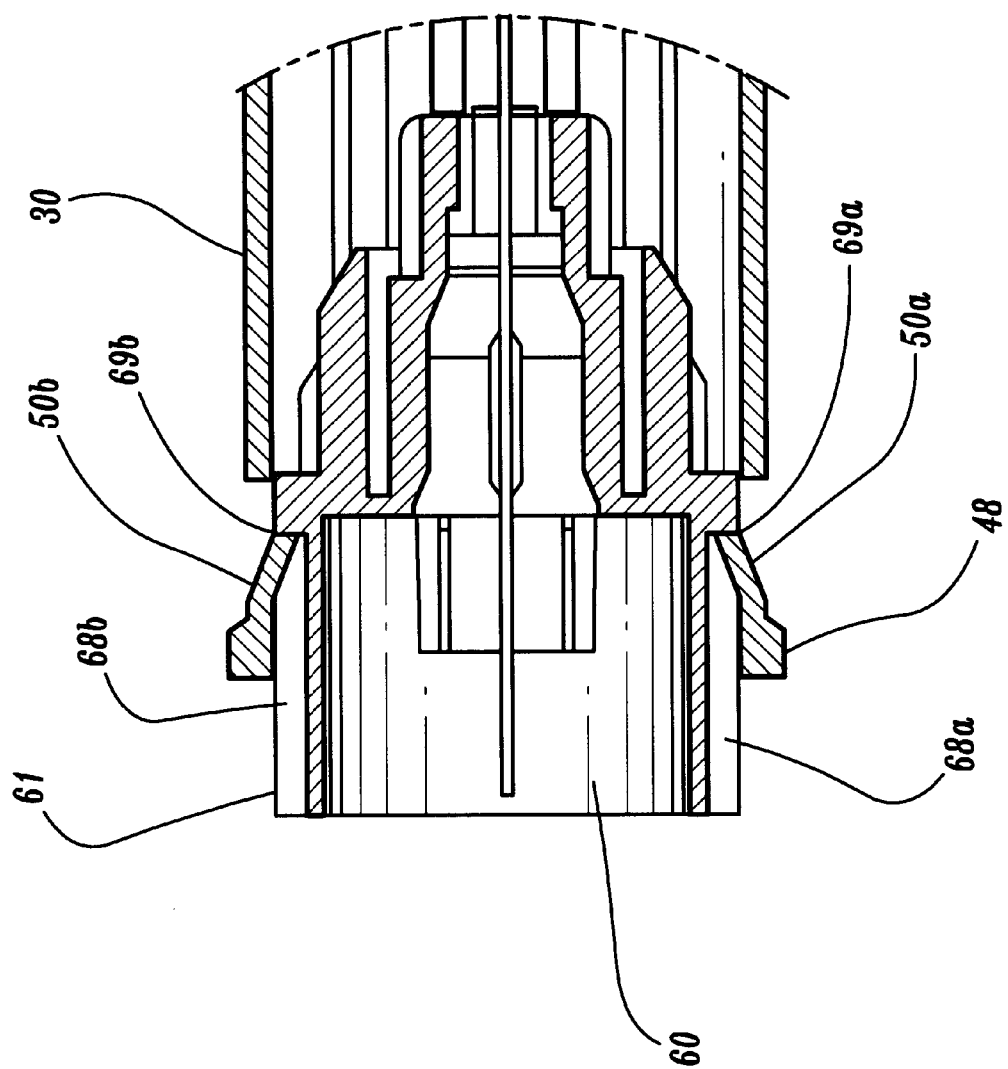
FIG. 4A is a bottom cross-sectional view of the proximal portion of the needle cannula apparatus shown in FIG. 4.

Referring to FIG. 4A, proximal hub portion 61 further includes diametrically spaced tab slots 68a and 68b. Tab slots 68a and 68b extend from a proximal end of proximal hub portion 61 to tab slot ends 69a and 69b. Tab slots 68a and 68b slidingly engage respective tab stops 50a and 50b of outer shield 30 so that tab stops 50a and 50b abut slot ends 69a and 69b to limit travel of outer shield 30 thereby defining a distal position of shield 30. It is envisioned that varying numbers of tab slots and a corresponding number of tab stops may be used.

Referring back to FIGS. 2 and 2A, a cantilevered portion 66, extending distally from proximal hub portion 61, is formed by a pair of through slots 67 which extend into proximal hub portion 61 from a distal end thereof. Intermediate crown portion 76 extends distally from proximal hub portion section 61 and includes a flattened top portion 74 for accommodating radially directed inward cantilevered movement of cantilevered section 66. Cantilevered section 66 accommodates a button member such as, for example, a radially extending pedestal member 62 and a transverse button 64 formed at a distal portion thereof. Pedestal member 62 and transverse button 64 form a manipulable portion of needle hub 60. Transverse button 64 provides a large area for increased accessibility and visibility. Alternatively, pedestal member 62 and transverse button 64 may have other configurations or have portions omitted without departing from the scope and spirit of the present disclosure.

A hub stop, such as, for example, a raised stop 72, having greater transverse width than pedestal member 62, protrudes radially from and is formed at a distal end of cantilevered section 66, distal to pedestal member 62. As will be discussed herein, raised stop 72 is resiliently biased by cantilevered section 66 against the inner periphery of outer shield 30. Upon longitudinal sliding motion of shield 30 relative to needle hub 60, raised stop 72 slides against the inner periphery of outer shield 30 and below shield slot 32. It is contemplated that raised stop 72 may slide above shield slot 32.

During longitudinal motion, pedestal member 62 extends through shield slot 32, due to its narrow configuration, relative to transverse button 64. When outer shield 30 is in a transport position, discussed below, raised stop 72 is allowed to extend radially outward into transport enlarged slot section 42. Raised stop 72 is biased into transport enlarged slot section 42 where it abuts the circumferential wall of outer shield 30, thereby preventing further longitudinal motion of outer shield 30. Outer shield 30 is prevented from longitudinal movement by interference with raised stop 72, until a practitioner radially depresses transverse button 64. Inward radial pressure applied by a practitioner to pedestal member 62 and/or transverse button 64 disengages raised stop 72 from transport enlarged slot section 42, enabling longitudinal motion of outer shield 30.

From the transport position, further distal longitudinal movement of outer shield 30 to a distal position (FIG. 4), discussed below, allows raised stop 72 to extend into proximal enlarged slot section 46 (FIG. 1), thereby preventing proximal retraction of outer shield 30. Distal movement of outer shield 30 is prevented by engagement of tab stops 50a and 50b with tab slot ends 69a (FIG. 4A) and 69b, respectively. When outer shield 30 is in the distal position, pedestal member 62 and transverse button 64 are overlapped by button cover 40, thereby preventing a practitioner from disengaging raised stop 72 from enlarged slot section 46.

Alternative embodiments within the scope and spirit of the present disclosure may include a shield slot 32 having more than two enlarged slot sections 42 and 46 so as to provide incremental extension and retraction of outer shield 30 and to expose alternative lengths of a needle cannula 90. Still further embodiments may include internally protruding features (not shown) rather than enlarged slot sections 42 and 46 and alternative mating stop features (not shown) that are biased to engage the internally protruding features and effect a releasable and a permanent latched position.

Figure 3:
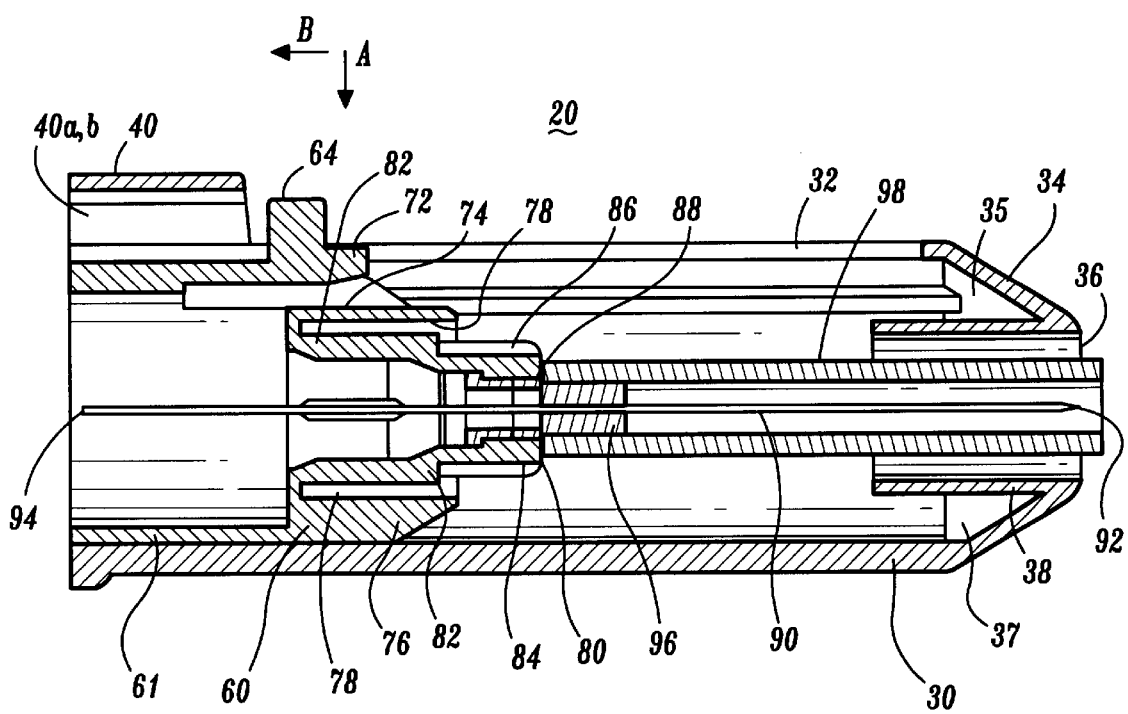
FIG. 3 is an enlarged side cross-sectional view of the needle cannula apparatus shown in FIG. 1.

Referring to FIG. 3, inner needle hub 60 is slidingly engaged within outer shield 30. Intermediate crown portion 76 includes an inner cylindrical cut-out 78 which is configured and dimensioned to receive inner cylindrical section 38 of outer shield 30. In addition to providing a needle guiding and straightening function, inner cylindrical section 38 forms a moisture barrier, discussed below, when it is engaged with inner cylindrical cut-out 78. Hub distal crown portion 80 includes raised rail portions 86 which correspond and fit with an inner radius of inner cylindrical section 38, discussed below.

Figure 6:
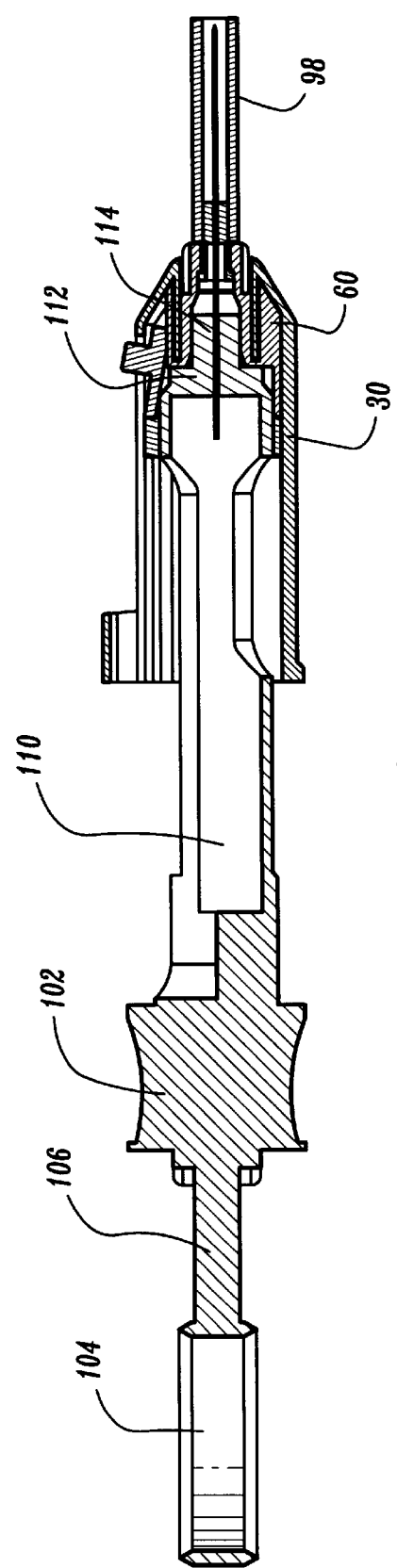
FIG. 6 is a side cross-sectional view, in part elevation, of the needle cannula apparatus and instrument shown in FIG. 5 having the protective guard disposed thereon.

Intermediate crown portion 76 includes an inner threaded or self-threaded portion 82 for receiving a threaded syringe tip 112 (FIG. 6). Distal crown portion 80, intermediate crown portion 76 and proximal crown portion 61 define, a centrally disposed lumen 88 formed therethrough which is used to house and affix needle cannula 90 of needle hub 60. Although a threaded attachment to syringe tip 112 is described and illustrated, any number of fastening means including snap arms, annular snap rings, self-threading features, adhesives, etc., may be used to attach cannula needle hub 60 to syringe tip 112 without departing from the scope and spirit of the present disclosure.

Referring to FIG. 4, needle cannula 90 includes both a distal penetrating end 92 configured to penetrate the skin of a subject and a proximal end 94 configured to receive a cartridge or other vessel containing preventive medications, medicaments, etc., such as CARPULE® brand cartridges manufactured by Cook-Waite Laboratories, Inc. Needle cannula 90 is securely affixed to lumen section 88 of distal crown portion 80 of inner needle hub 60 with bonding mechanism (adhesive, metal insert, etc.). Needle cannula 90 is inserted into inner needle hub 60 and secured by a bonding feature such as, for example, a metal insert, epoxy, adhesive, etc. Needle cannula 90 may be protectively housed within a needle sheath 98 (FIG. 3) which would be removable upon use of shielded safety needle 20.

Shielded safety needle 20 is assembled by inserting inner needle hub 60 into outer shield 30. Tab stops 50a and 50b are deflected radially outward by engagement with inner needle hub 60 during assembly. Tab stops 50a and 50b bias radially inward upon clearing intermediate crown portion 76 into outer shield 30. Upon sufficient travel of inner needle hub 60, tab slot ends 69a and 69b are displaced beyond tab stops 50a and 50b. Shielded safety needle 20 is placed in a transport position (FIG. 3) for safe handling and installation with a syringe.

Outer shield 30 has a range of movement relative to inner needle hub 60 between a distal position (FIG. 4) and a proximal position (FIG. 5), which includes a transport position (FIG. 3). In the distal position, pedestal member 62 and transverse button 64 are fixedly lockable with proximal enlarged slot section 46 and is enclosed by button cover 40. The practitioner is shielded from both distal penetrating end 92 and proximal end 94 of needle cannula 90 in this position.

In the transport position, pedestal member 62 and transverse button 64 are releasably lockable with transport enlarged section 42. The practitioner is also shielded from both distal penetrating end 92 and proximal end 94 in this position.

In the proximal position, distal penetrating end 92 is fully extended from distal opening 36 of outer shield 30. Shielded safety needle 20 can also employ alternative structure to compensate for different needle lengths. Further, it is contemplated that outer shield 30 may be manufactured at different lengths, all of these designs being configured to accommodate a standard inner needle hub 60 configured for the various embodiments of shielded safety needle 20. During use, a practitioner receives shielded safety needle 20 packaged in the transport position.

Figure 5:
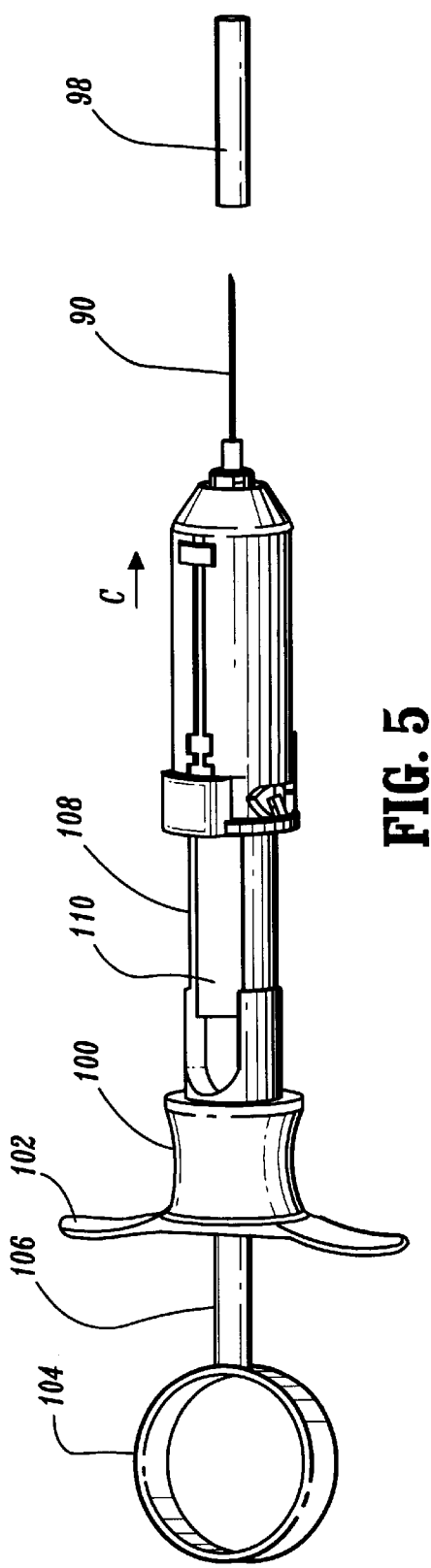
FIG. 5 is a top perspective view illustrating the needle cannula apparatus shown in FIG. 1 mounted to an instrument having a protective guard separated therefrom.

Referring now to FIGS. 5 and 6, shielded safety needle 20 is attached to a syringe 100 by threading inner needle hub 60 onto a threaded extension member 114 of syringe 100. Referring back to FIG. 3, once attached, the practitioner activates needle cannula 90 by depressing transverse button 64 of inner needle hub 60 radially inward, in the direction shown by arrow A, so that the top edge of raised stop 72 moves below the inner peripheral surface of outer shield 30. Once transverse button 64 is depressed, outer shield 30 may be moved in a proximal axial direction along longitudinal axis x, in the direction shown by arrow B, thus exposing distal penetrating end 92 of needle cannula 90.

A friction fit between distal crown portion 80 and intermediate crown portion 76 of inner needle hub 60 and inner cylindrical section 38 of outer shield 30 retains outer shield 30 in the distal position during use. The friction fit may be provided between raised rails 86 and inner cylindrical section 38 and/or between inner cylindrical section 38 and peripheries of inner cylindrical cut-out 78. Once outer shield 30 has been retracted into the proximal position and a cartridge is inserted, the practitioner may remove tubular sheath 98 from needle cannula 90. Needle cannula 90 is thereby placed in an active position and prepared for the administration of injections, etc.

After administering injections, the practitioner may push outer shield 30 in a distal axial direction along longitudinal axis x, in the direction shown by arrow C in FIG. 5, until it automatically stops in the releasably retained transport position. Depressing pedestal member 62 and/or transverse button 64 is not required to slide outer shield 30 into the transport position. From the transport position, the practitioner may depress pedestal member 62 and/or transverse button 64 and slide outer shield 30 in the proximal axial direction to expose cannula needle 90 for additional injections. Alternatively, the practitioner may depress pedestal member 62 and/or transverse button 64 and slide outer shield 30 in the distal axial direction to lock outer shield 30 in the distal position. It is envisioned that the practitioner need not depress pedestal member 62 and/or transverse button 64, but simply pull outer shield 30 distally.

In the distal position, pedestal member 62 and transverse button 64 are engaged with proximal enlarged slot section 46. Pedestal member 62 and transverse button 64 are enclosed by button cover 40. Button cover 40 advantageously prevents disengagement of pedestal member 62 and transverse button 64 from proximal enlarged slot section 46 by enclosure thereof. Shielded safety needle 20 is fixedly locked and pedestal member 62 and transverse button 64 cannot be depressed to further expose needle cannula 90. Other configurations alternative to button cover 40 are contemplated to facilitate locking shielded safety needle 20.

The operative prescribed steps involved with proper use of shielded safety needle 20, according to the present disclosure will now be discussed. The procedures and methods described below will discuss a method of safely and effectively administering an injection using shielded safety needle 20. It can be seen that shielded safety needle 20, according to the present disclosure, is operable with the use of one hand. Needle cannula 90 can be placed in the safe or distal position by using an extended finger to push the proximal end of outer shield 30 in the distal longitudinal direction.

Referring to FIGS. 3–6, shielded safety needle 20 is mounted to syringe 100. Syringe tip 112 includes a threaded extension member 114 for threadingly engaging corresponding threads of inner threaded portion 82 of inner lumen 88. Alternatively, threaded extension member 114 engages an inner portion 82 which is self-threading at intermediate crown portion 76. Syringe 100 may include an extending handle member 102. Syringe 100 also includes a housing 108 having a hollow housing interior 110 for which cartridges containing preventive medicines, medicaments, anesthetics, etc., are inserted. An actuator 106 and actuator ring 104 are slidingly received within handle member 102 and the interior of housing 110. Upon distal actuation of actuator ring 104 and actuator 106, a tip (not shown) of actuator 106 provides movement to an internal piston of the cartridge which causes the medicament therein to be pressurized and subsequently propelled through proximal end 94 of needle cannula 90 which is disposed within a distal portion of the cartridge.

Upon assembly of shielded safety needle 20 with syringe 100, shielded safety needle 20 is ready for use by the practitioner. Needle cannula 90 is completely housed within outer shield 30 and raised hub stop 72 is disposed in transport enlarged slot section 42 which coincides with the transport position (FIG. 3) of shielded safety needle 20. Upon actuation of transverse button 64 in a radial direction (in the direction shown by arrow A in FIG. 3), raised stop 72 of cantilevered section 66 is positioned below and beyond the circumferential wall of inner shield 30 and, therefore, allows outer shield 30 to be slid in both proximal (shown by arrow B in FIG. 3) and distal (shown by arrow C in FIG. 5) axial directions with respect to inner needle hub 60 and syringe 100. The practitioner may easily determine if shielded safety needle 20 is in the distal position (FIG. 4) or releasably retained in the transport position (FIG. 3) by visual inspection of the location of transverse button 64 and/or pedestal member 62 with respect to its position along shield slot 32.

Figure 7:
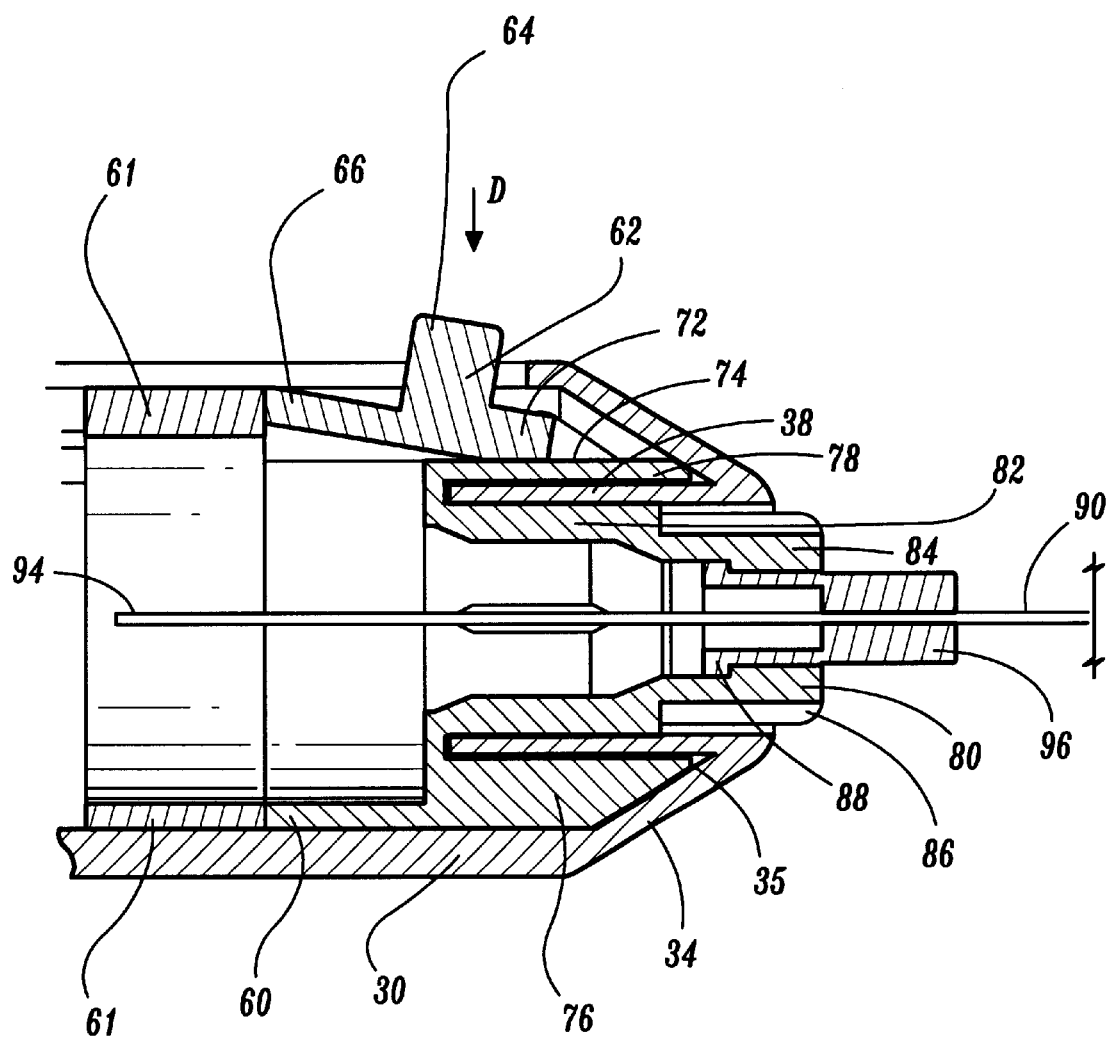
FIG. 7 is an enlarged, side cross-sectional view illustrating a distal portion of the needle cannula apparatus shown in FIG. 1 in the distal position.

Initially, outer shield 30 is in the transport position (FIG. 3), discussed above. Outer shield 30 is proximally retracted to the proximal position, as discussed with regard to FIG. 5, so that needle cannula 90 is fully extended in a ready-to-use position. Referring to FIG. 7, in the proximal position, transverse button 64, raised stop 72 and cantilevered section 66 are abutted in an inward radial direction, in the direction shown by arrow D, against flattened portion 74 and positioned within upper crown portion 35 within the inner chamber of outer shield 30.

Distal crown member 84 protrudes through shield crown opening 36 of shield crown 34 to thereby expose needle cannula 90. Outer shield 30 is held in this ready-to-use position at least in part through the frictional forces between the inner periphery of inner cylindrical section 38 and inner cylindrical cutout 78 of inner needle hub 60.

Mating engagement of inner cylindrical section 38 and inner cylindrical cut-out 78 forms an interference fit therebetween to substantially prevent collection of substances that impair the transparency of outer shield 30. This barrier between outside matter and the inner chamber area of outer shield 30 and inner needle hub 60 advantageously maintains a visual indication of the status of the medicament being dispensed from shielded safety needle 20. Exposure of inner crown 30 to moisture or fluid, during use of shielded safety needle 20, is thereby avoided.

Inner cylindrical section 38 extends into outer shield 30 serving as a moisture barrier when outer shield 30 is retracted and needle cannula 90 is exposed. Moisture from the subject's mouth becomes trapped within the outer shield 30/inner hub 60 interface. The moisture path from the patient's mouth to the inside of outer shield 30 is blocked, therefore, the occurrence of outer shield 30 fogging is substantially eliminated.

Once the injection has been administered, the practitioner provides a distally directed force to outer shield 30, shown by arrow C in FIG. 5, thereby overcoming the frictional forces between the interference fit of inner cylindrical section 38 with inner cylindrical cut-out 78. Continued distal movement of outer shield 30 with respect to needle hub 60 and syringe 100 causes raised stop 72 to rest in the transport position, i.e., the initial position described hereinabove.

Outer shield 30 is retractable from the transport position (FIG. 3) to the proximal position (FIG. 5) to administer additional injections of medicament to a subject. Alternatively, when no further injections are needed, the practitioner may apply an inward radial force, in the direction shown by arrow D in FIG. 7, to transverse button 64 lowering raised stop 72 of cantilevered section 66 toward flattened portion 74. Outer shield 30 is free to axially move with respect to inner needle hub 60.

Continued distally directed movement of outer shield 30 positions transverse button 64 and correspondingly outer shield 30 in the distal position (FIG. 4). This locks outer shield 30 within the confines of button cover 40. In the locked position, pedestal member 62 of cantilevered section 66 is substantially aligned with the surfaces of narrow area 44 of shield slot 32. Outer shield 30 is prevented from proximal movement by engagement of raised stop 72 with proximal enlarged slot section 46. Access by the practitioner to button member 64 is restricted, by button cover 40, discussed above, thus disabling any further uses of shielded safety needle 20.

Referring back to FIG. 4A, any further distally directed movement of outer shield 30 with respect to inner needle hub 60 is prohibited by tab stops 50a and 50b. Tab stops 50a and 50b are slidingly engaged within tab slots 68a and 68b and abut respective tab slot ends 69a and 69b. In this position, distal end 92 of needle cannula 90 is protectively housed by outer shield 30. Proximal end 94 of needle cannula 90 is protectively housed by proximal hub portion 61 of inner needle hub 60. To discard shielded safety needle 20, outer shield 30 is unthreaded from syringe 100 and discarded.

It will be understood that various modifications may be made to the embodiments disclosed herein. Therefore, the above description should not be construed as limiting but merely as exemplification of preferred embodiments. Those skilled in the art will envision other modifications within the scope and spirit of the claims appended hereto.

What is claimed is:

1. A needle cannula apparatus comprising:
a needle hub being mountable to an instrument and including a cantilevered portion extending therefrom, the cantilevered portion having a button member and a hub stop disposed at a distal end thereof, the needle hub defining at least one tab slot having a tab slot end; and
a shield being movably disposed about the needle hub and defining a shield slot configured for relative slidable movement of the button member therein, the shield slot including a proximal enlarged slot section configured to engage the hub stop such that proximal movement of the shield is prevented, the shield further including at least one tab stop being configured for movement within the at least one tab slot of the needle hub and engagement with the tab slot end such that distal movement of the shield is prevented.

2. A needle cannula apparatus according to claim 1, wherein the needle hub includes a needle cannula coaxially mounted therewith.

3. A needle cannula apparatus according to claim 1, wherein the needle hub includes a proximal portion defining an aperture having an internally threaded portion configured for releasably mounting the instrument therewith.

4. A needle cannula apparatus according to claim 1, wherein the needle hub includes a proximal portion defining an aperture having a self-threading portion configured for releasably mounting the instrument therewith.

5. A needle cannula apparatus according to claim 1, wherein the needle cannula hub includes at least one hub slot and the shield includes at least one shield rail, the at least one shield rail slidably engaging the at least one hub slot facilitating axial movement of the shield relative to the needle hub.

6. A needle cannula apparatus according to claim 5, wherein the needle hub has three hub slots and the shield has three corresponding shield rails.

7. A needle cannula apparatus according to claim 1, wherein the needle hub defines two diametrically spaced tab slots and the shield further includes two diametrically spaced tab stops.

8. A needle cannula apparatus according to claim 1, wherein the proximal enlarged slot section of the shield slot is defined at a proximal portion thereof and the shield slot further defines a transport enlarged slot section disposed between a distal portion of the shield slot and the proximal enlarged slot section.

9. A needle cannula apparatus according to claim 8, wherein the transport enlarged slot section is configured to releasably engage the hub stop such that axial movement of the shield is prevented.

10. A needle cannula apparatus according to claim 9, wherein the button member is manipulable to facilitate release of the hub stop from engagement with the transport enlarged slot section facilitating axial movement of the shield.

11. A needle cannula apparatus according to claim 8, wherein the shield has a range of movement between a distal position whereby a distal end of the needle hub is shielded and a proximal position whereby the distal end of the needle hub is fully extended.

12. A needle cannula apparatus according to claim 11, whereby in the distal position the hub stop engages the proximal enlarged slot section such that proximal movement of the shield is prevented.

13. A needle cannula apparatus according to claim 11, wherein the range of movement includes a transport position whereby the transport enlarged slot section is configured to engage the hub stop such that axial movement of the shield is prevented.

14. A needle cannula apparatus according to claim 13, wherein the button member is manipulable to release the hub stop from the transport enlarged slot section facilitating axial movement of the shield.

15. A needle cannula appartus according to claim 1, wherein the shield has a range of movement between a distal position whereby a distal end of the needle hub is shielded and a proximal position whereby the distal end of the needle hub is fully extended.

16. A needle cannula apparatus according to claim 15, wherein the needle hub and the shield engage to maintain the shield in the proximal position by a friction fit formed therebetween.

17. A needle cannula apparatus according to claim 1, wherein the shield has an inner surface formed at a distal portion thereof, the inner surface being configured to engage a distal end of the needle hub to facilitate coaxial alignment of the distal end of the needle hub with the shield.

18. A needle cannula apparatus according to claim 17, wherein the inner surface is configured to guide and straighten a needle cannula of the needle hub.

19. A needle cannula apparatus according to claim 1, wherein the needle hub and the shield engage to maintain the shield in the proximal position by a friction fit formed therebetween. substantially transparent material.

20. A needle cannula apparatus according to claim 19, wherein the shield has an inner surface formed at a distal portion thereof, the inner surface engaging the needle hub in a configuration to substantially prevent collection of substances that impair the transparency of the shield.

21. A needle cannula apparatus according to claim 1, wherein the shield includes a button cover disposed about the proximal enlarged slot section and being configured to prevent disengagement of the hub stop and the proximal enlarged slot section.

22. A needle cannula apparatus comprising:

a needle hub having a needle cannula coaxially mounted therewith and an engagement portion configured for releasably mounting the needle hub with an instrument, the needle hub including at least one hub slot and at least one tab slot defined in an outer surface of the needle hub, the at least one tab slot having a tab slot end, the needle hub further including a button member extending therefrom, the button member having a hub stop; and a shield being slideably engageable with the needle hub, the shield including at least one shield rail being configured for slidable engagement with the at least one hub slot of the needle hub such that the shield and the needle hub are relatively movable, the shield further including at least one tab stop being configured for movement within the at least one tab slot and engageable with the tab slot end, the shield defining a shield slot axially extending along at least a portion thereof, the shield slot including a proximal enlarged slot section adjacent a proximal portion of the shield and a transport enlarged slot section being distally disposed relative to the proximal enlarged slot section, the shield slot configured for relative slidable movement of the button member therein, wherein the shield has a range of movement relative to the needle hub between a distal and a proximal position and including a transport position, in the distal position the button member is fixedly lockable with the proximal enlarged slot section due to the engagement of the hub stop therewith, in the transport position the button member is releasably lockable with the transport enlarged slot section due to the engagement of the hub stop therewith and in the proximal position a distal portion of the needle cannula is fully extended from a distal opening of the shield.

23. A needle cannula apparatus according to claim 22, wherein the shield further defines a cover portion extending therefrom which is configured to enclose at least a portion of the proximal enlarged slot section in the distal position of the shield.

24. A needle cannula apparatus according to claim 22, wherein the needle hub and the shield engage to maintain the shield in the proximal position by a friction fit formed therebetween.

25. A needle cannula apparatus according to claim 22, wherein the shield has an inner surface formed at a distal portion thereof, the inner surface being configured to engage a distal end of the needle hub to facilitate coaxial alignment of the distal end of the needle hub with the shield.

26. A needle cannula apparatus according to claim 25, wherein the inner surface is configured to guide and straighten a needle cannula.

27. A needle cannula apparatus according to claim 22, wherein the shield is fabricated from a substantially transparent material and has an inner surface formed at a distal portion thereof, the inner surface engaging the needle hub in a configuration to substantially prevent collection of substances that impair the transparency of the shield.

* * * * *